(12) United States Patent
Guile et al.

(10) Patent No.: US 6,713,483 B1
(45) Date of Patent: Mar. 30, 2004

(54) [1,2,3]-TRIAZOLO[4,5-D] PYRIMIDINE COMPOUNDS

(75) Inventors: Simon Guile, Loughborough (GB); Brian Springthorpe, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/130,194

(22) PCT Filed: Nov. 14, 2000

(86) PCT No.: PCT/SE00/02229

§ 371 (c)(1),
(2), (4) Date: May 13, 2002

(87) PCT Pub. No.: WO01/36421

PCT Pub. Date: May 25, 2001

(30) Foreign Application Priority Data

Nov. 15, 1999 (SE) ................................ 9904129

(51) Int. Cl.[7] ..................... A61K 31/519; C07D 487/04
(52) U.S. Cl. ..................... 514/261.1; 544/254
(58) Field of Search ........................ 544/254; 514/261.1

(56) References Cited

U.S. PATENT DOCUMENTS 6,525,060 B1   2/2003   Hardern et al. ............. 514/258

FOREIGN PATENT DOCUMENTS

| WO | 9703084 | 1/1997 |
| WO | 9828300 | 7/1998 |
| WO | 9905142 | 2/1999 |
| WO | 9905143 | 2/1999 |
| WO | 9941254 | 8/1999 |
| WO | 0004021 | 1/2000 |

*Primary Examiner*—John M. Ford
(74) *Attorney, Agent, or Firm*—White & Case LLP

(57) ABSTRACT

The invention provides [1,2,3]-triazolo[4,5-d]pyrimidine analogue compounds of formula (I)

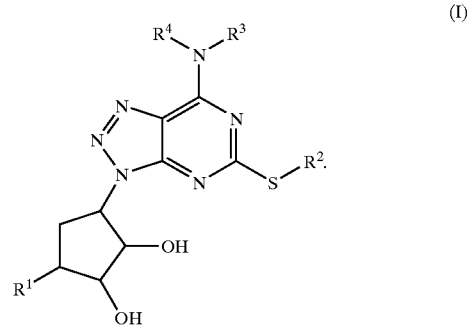

The invention is also directed to pharmaceutical compositions containing the compounds, processes for the preparation of the compounds and methods of treatment employing the compounds.

20 Claims, No Drawings

[1,2,3]-TRIAZOLO[4,5-D] PYRIMIDINE COMPOUNDS

FIELD OF THE INVENTION

The present invention provides novel [1,2,3]-triazolo[4,5-d]pyrimidine analogues, their use as medicaments, compositions containing them and processes for their preparation.

BACKGROUND OF THE INVENTION

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and platelet-mediated occlusion or re-occlusion also compromises angioplasty.

A number of converging pathways lead to platelet aggregation. Whatever the initial stimulus, the final common event is a cross-linking of platelets by binding of fibrinogen to a membrane-binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–30 1637; Neuhaus K. L. et. al. (1994) *Circulation* 90, pp. 1638–1642).

It has been found that adenosine 5'-diphosphate (ADP) acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor. The pharmacological characteristics of this receptor have been described, for example, in the references by Humphries et al., *Br. J. Pharmacology*, (1994), 113, 1057–1063, and Fagura et al., *Br. J. Pharmacology* (1998) 124, 157–164. Recently it has been shown that antagonists at this receptor offer significant improvements over other anti-thrombotic agents (see *J. Med Chem*. (1999) 42, 213). There is a need to find $P_{2T}$ ($P2Y_{ADP}$ or $P2T_{AC}$) antagonists as anti-thrombotic agents.

DESCRIPTION OF THE INVENTION

In a first aspect the invention provides a compound of formula (I):

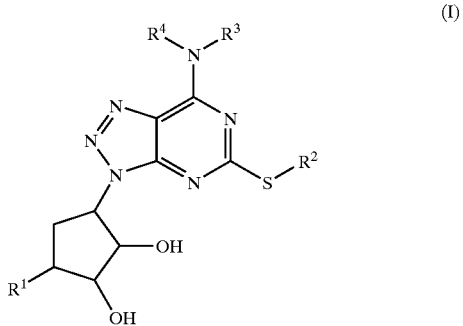

(I)

wherein:
$R^1$ is $OR^5$ or $CH_2R^6$;
$R^2$ is alkyl $C_{1-6}$ or haloalkyl $C_{1-6}$;
$R^3$ is cycloalkyl $C_{3-6}$, optionally substituted by $R^7$;
$R^4$ is alkyl $C_{1-6}$;
$R^5$ is H or alkyl $C_{1-6}$, optionally substituted by OH;
$R^6$ is OH, $N_3$, or $NHR^8$;
$R^7$ is phenyl, optionally substituted by one or more groups selected from alkyl $C_{1-6}$, halogen, and $OR^{10}$;
$R^8$ is H, alkyl $C_{1-6}$, or $COR^9$;
$R^9$ is alkyl $C_{1-6}$;
$R^{10}$ is alkyl $C_{1-6}$;
or a pharmaceutically acceptable salt or solvate thereof, or a solvate of such a salt.

Preferably the compound of formula (I) has the following stereochemistry:

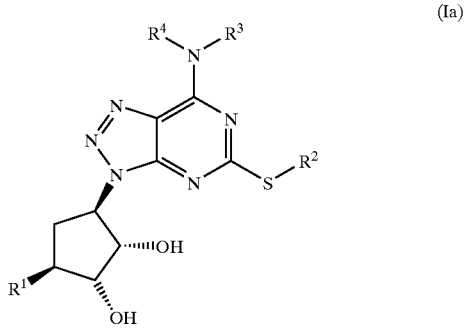

(Ia)

Where $R^3$ is

the stereochemistry is preferably

Suitably $R^1$ is OH, $O(CH_2)_2OH$, $CH_2OH$, $CH_2N_3$, $CH_2NH_2$, or $CH_2NHAc$.
Suitably $R^2$ is n-Pr.
Suitably $R^3$ is cyclopropyl optionally substituted with phenyl, optionally substituted by one or more groups selected from alkyl $C_{1-6}$, halogen and $OR^{10}$.

Suitably $R^4$ is methyl.

Particularly preferred compounds of the invention include:

[1S-[1α,2α,3β,5β(1S*, 2R*)]]-3-(2-Hydroxyethoxy)-5-[7-[N-methyl-(2-phenylcyclopropyl)amino]-5-(propylthio)-3H-[1,2,3]-triazolo[4,5-d]pyrimidin-3-yl]cyclopentane-1,2-diol;

[1S-[1α,2β,3β,4α(1S*, 2R*)]]4-[7-[N-Methyl-(2-phenylcyclopropyl)amino]-5-(propylthio)-3H-[1,2,3]-triazolo[4,5-d]pyrimidin-3-yl]cyclopentane-1,2,3-triol;

[1S-[1α,2α,3β,5β(1S*,2R*)]]-3-(Hydroxymethyl)-5-[7-[N-methyl-(2-phenylcyclopropyl)amino]-5-(propylthio)-3H-[1,2,3]-triazolo[4,5-d]pyrimidin-3-yl]cyclopentane-1,2-diol;

[1S-[1α,2β,3β,4α(1S*,2R*)]]-4-[7-[N-[2-(3,4-Difluorophenyl)cyclopropyl]-N-methylamino]-5-(propylthio)-3H-[1,2,3]-triazolo[4,5-d]pyrimidin-3-yl]cyclopentane-1,2,3-triol;

[1S-[1α,2β,3β,4α(1S*,2R*)]]4-[7-N-[2-(4Methoxyphenyl)cyclopropyl]-N-methylamino]-5-(propylthio)-3H-[1,2,3]-triazolo[4,5-d]pyrimidin-3-yl]cyclopentane-1,2,3 -triol;

[1S-[1α,2α,3β,5β(1S*,2R*)]]-3-Azidomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol;

[1S-[1α,2α,3β,5β(1S*,2R*)]]-3-Aminomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol;

[1R-[1α,2α,3β,4α(1R*,2S*)]]-N-[[2,3-Dihydroxy4-[7-[N-methyl-(2-phenylcyclopropyl)amino]-5-(propylthio)-3H-[1,2,3]-triazolo[4,5-d]pyrimidin-3-yl]cyclopentyl]methyl]acetamide;

or a pharmaceutically acceptable salt or solvate thereof, or a solvate of such a salt.

According to the invention there is further provided a process for the preparation of a compound of formula (I) which comprises:

a. For compounds of formula (I) where $R^1$ is O(CH$_2$)$_2$OH, the reaction of a compound of formula(II)

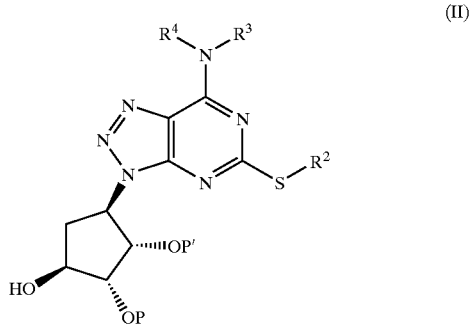

(II)

where $R^2$, $R^3$ and $R^4$ are defined in formula (I). P and P' are protecting groups, for example CMe$_2$, with 2-(2-bromoethoxy)-2H-tetrahydropyran, in the presence of dimethylsulphoxide and a phase transfer catalyst, such as a tetra-alkylammonium halide, preferably tetra-butylammonium bromide, and aqueous sodium hydroxide, in the presence of a water-immiscible organic solvent, preferably toluene, at a temperature of between about 50 and about 120° C., and optionally thereafter removing any protecting groups.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Tetrahydropyranyl groups can be removed by the use of an acid, for example, trifluoroacetic acid, in water or aqueous acetonitrile, at a temperature between about 20 and about 50° C.

A compound of formula (II) can be prepared by reacting a compound of formula (III)

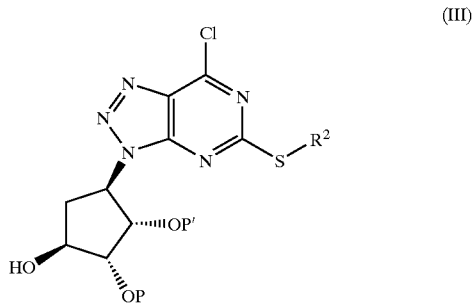

(III)

where P, P', $R^2$ are defined above, with $R^3R^4NH$, in the presence of a base, preferably N,N-di-isopropylethylamine, in an inert ethereal solvent, preferably diethyl ether or tetrahydrofuran or a chlorocarbon solvent, preferably dichloromethane, at a temperature of between about 20 and about 50° C.

Where $R^3R^4NH$ is

and $R^7$ is phenyl, the compound may be prepared as described by C. Kaiser et al, J. Org. Chem., 1962, 27, 768–773, using (1R-trans)-2-phenylcyclopropanamine, [R-(R*,R*)]-2,3-dihydroxybutanedioate (1:1) (prepared as described by L. A. Mitscher et al, J. Med. Chem., 1986, 29, 2044).

Where $R^3R^4NH$ is

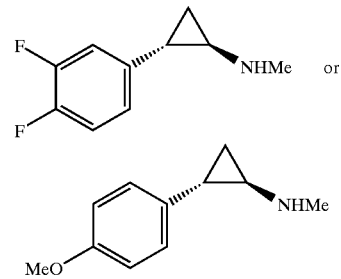

such compounds can be prepared by acylation of

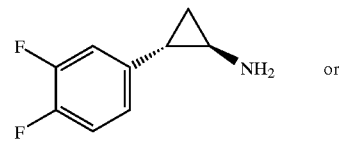

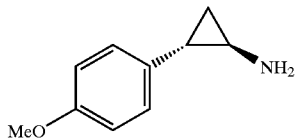

(prepared as described in International Patent Application WO 9905143) with acetic anhydride and potassium carbonate in tetrahydrofuran, at a temperature of between about 20 and about 50° C. The product of this reaction can be methylated with sodium hydride and methyl iodide in tetrahydrofuran, at a temperature of between about 20 and about 50° C., followed by deacylation with aqueous hydrochloric acid, at a temperature of between about 20 and about 100° C.

A compound of formula (III) can be prepared by diazotising a compound of formula (IV)

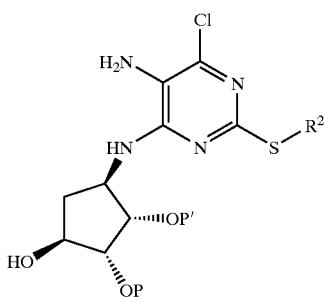

where P, P' and $R^2$ are defined above, with an alkyl nitrite, preferably iso-amylnitrite, in an inert dipolar aprotic solvent, preferably acetonitrile, at a temperature between about 50 and is about 100° C.

A compound of formula (IV) can be prepared by reducing a compound of formula (V),

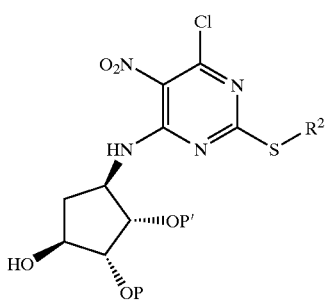

where P, P' and $R^2$ are defined above, using a metal, preferably iron powder, in the presence of an acid, preferably acetic acid, at a temperature between about 20 and about 50° C.

A compound of formula (V) can be prepared by reacting a compound of formula (VI),

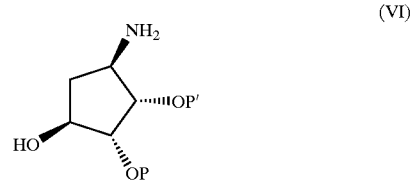

where P and P' are defined above, with a compound of formula (VII):

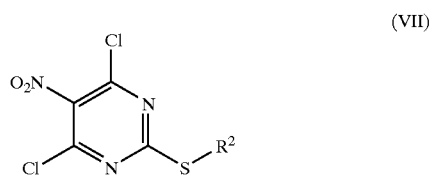

where $R^2$ is defined above, in the presence of a base, preferably N,N-di-isopropylethylamine, in an inert ethereal solvent, preferably tetrahydrofuran, at a temperature between about 20 and about 50° C.

Where $R^2$ is n-Pr, the compound of formula (VII) can be prepared as described in International Patent Application WO 9703084.

A compound of formula (VI) can be prepared by reacting a compound of formula (VIII),

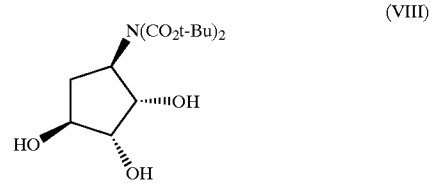

with a ketal or acetal, preferably 2,2-dimethoxypropane, in acetone as solvent, in the presence of an acid, preferably p-toluenesulphonic acid, at a temperature of between about 20 and about 50° C., followed by hydrolysis and decarboxylation of the protected iminodiester under aqueous conditions, preferably in water, at a temperature of between about 100 and about 120° C.

A compound of formula (VIII) can be prepared by dihydroxylating a compound of formula (IX),

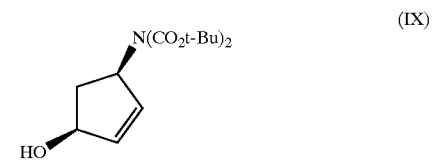

using osmium tetroxide, in the presence of an oxidising agent, preferably N-methylmorpholine-N-oxide, under aqueous conditions, preferably in aqueous tetrahydrofuran, at a temperature between about 20 and about 50° C.

A compound of formula (IX) can be prepared by reacting a compound of formula (X):

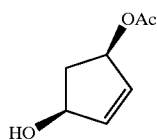
(X)

with a protected amine, preferably imidodicarbonic acid bis-(1,1-dimethylethyl)ester, in the presence of a base, preferably sodium hydride, and an organometallic catalyst, preferably tetrakis(triphenylphosphine)palladium(0), in an inert ethereal solvent, preferably tetrahydrofuran, at a temperature between about 20 and about 100° C.

b. For compounds of formula (I) where $R^1$ is OH, reacting a compound of formula (XI):

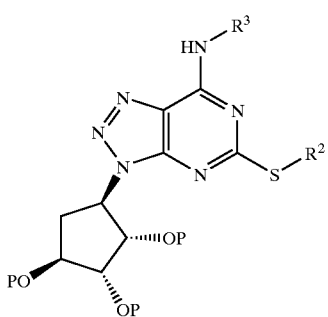
(XI)

where P is a protecting group and $R^2$ and $R^3$ are defined above, with a base, preferably sodium hydride, and an alkylating agent, preferably methyl iodide, in an inert dipolar aprotic solvent preferably N,N-dimethylformamide, at a temperature of between about 20 and about 50° C., and optionally thereafter removing any protecting groups Protecting groups include trialkylsilyl groups, preferably the t-butyldimethylsilyl group. This can be removed by reaction with a tetraalkylammonium fluoride, preferably tetrabutylammonium fluoride, under aqueous conditions, preferably aqueous tetrahydrofuran, at a temperature between about 20 and about 50° C.

A compound of formula (XI) can be made by reacting a compound of formula (XII):

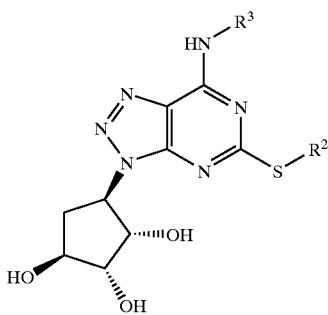
(XII)

where $R^2$ and $R^3$ are defined above with a trialkylsilylhalide, preferably t-butyldimethylsilylchloride, in the presence of imidazole, in an inert dipolar aprotic solvent, preferably N,N-dimethylformamide, at a temperature between about 20 and about 50° C.

A compound of formula (XII) can be made by reacting a compound of formula (XIII):

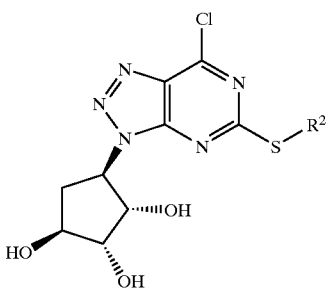
(XIII)

where $R^2$ is as defined in formula (I), with an amine $R^3NH_2$, in the presence of a base, preferably N,N-di-isopropylethylamine, in an inert ethereal solvent, preferably diethyl ether or tetrahydrofuran, at a temperature between about 20 and about 50° C.

Where $R^3NH_2$ is (1R-trans)-2-phenylcyclopropanamine, (1R-trans)-2-phenylcyclopropanamine, [R-(R*,R*)]-2,3-dihydroxybutanedioate (1:1) it may be prepared as described by L. A. Mitscher et al, J. Med. Chem., 1986, 29, 2044.

A compound of formula (XIII) can be made by reducing a compound of formula (XIV),

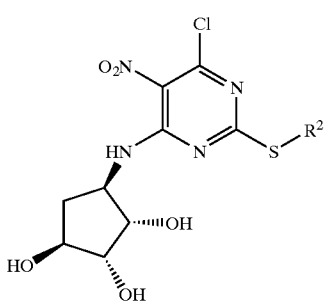
(XIV)

where $R^2$ is defined above, in the presence of a metal, preferably iron powder, and an acid, preferably acetic acid, at a temperature between about 20 and about 50° C., followed by diazotisation of the aminopyrimidine using an alkylnitrite, preferably iso-amylnitrite, in an inert dipolar aprotic solvent, preferably acetonitrile, at a temperature between about 50 and about 100° C.

A compound of formula (XIV) can be prepared by reacting a compound of formula (VII) with a compound of formula (XV)

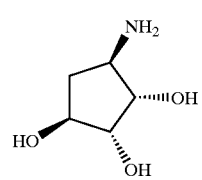
(XV)

in the presence of a base, preferably triethylamine or N,N-di-isopropylethylamine, in an inert ethereal solvent, preferably tetrahydrofuran, at a temperature between about 20 and about 100° C.

Compounds of formula (XV) can be prepared by the hydrolysis and decarboxylation of a compound of formula (VIII) using the methods described in step a.

c. For compounds of formula (I) where $R^1$ is $CH_2OH$ the reaction of a compound of formula (XVI)

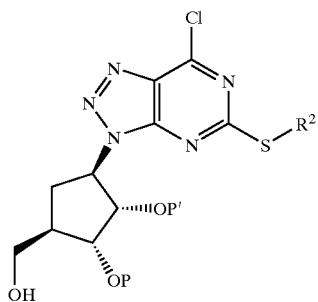

(XVI)

where $R^2$ is defined in formula (I), P and P' are protecting groups, with $R^3R^4NH$ and a base, preferably N,N-diisopropylethylamine, in a chlorocarbon solvent, preferably dichloromethane, at a temperature of between about 20 and about 50° C., and optionally thereafter removing any protecting groups.

The preparation of $R^3R^4NH$ is described above.

Where P and P' are $CMe_2$, the protecting groups can be removed using an acid under aqueous conditions, preferably using aqueous hydrochloric acid or aqueous trifluoroacetic acid in an alcoholic solvent, preferably methanol at a temperature between about 20 and about 50° C.

The preparation of a compound of formula (XVI), where P and P' are $CMe_2$, is described in International Patent Application WO 9703084.

d. For compounds of formula (I) where $R^1$ is $CH_2N_3$, the reaction of a compound of formula (XVII)

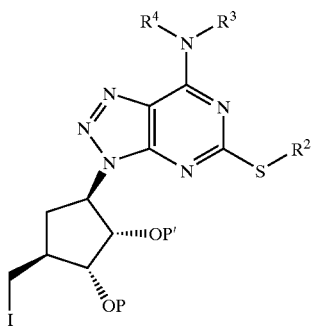

(XVII)

where $R^2$, $R^3$ and $R^4$ are defined in formula (I), and P and P' are protecting groups, with an alkali metal azide, preferably sodium azide, in an inert chlorocarbon solvent, preferably dichloromethane, at a temperature between about 20 and about 50° C., and optionally thereafter removing any protecting groups.

A compound of formula (XVII) can be made by reaction of a compound of formula (XVIII)

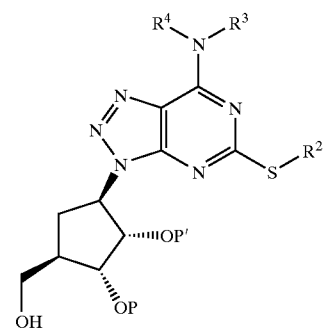

(XVIII)

where $R^2$, $R^3$ and $R^4$ are defined in formula (I), P and P' are protecting groups, with an iodinating agent, preferably methyltriphenoxyphosphonium iodide, in an inert chlorocarbon solvent, preferably dichloromethane, at a temperature between about 20 and about 50° C.

Compound (XVIII) can be prepared using the methods described in steps a–c.

e. For compounds of formula (I) where $R^1$ is $CH_2NH_2$, reduction of a compound of formula (I) where $R^1$ is $CH_2N_3$ (synthesised as described in step d), with hydrogen, in the presence of a transition metal catalyst, preferably 10% palladium on carbon, in an inert alcoholic solvent, preferably ethanol, at a temperature between about 20 and about 50° C., and optionally thereafter removing any protecting groups.

f. For compounds of formula (I) where $R^1$ is $CH_2NHCOR^9$, where $R^9$ is defined above, acylation of a compound of formula (I) where $R^1$ is $CH_2NH_2$ (synthesised as described in step e), with an acylating agent, preferably an acid anhydride $(R^9CO)_2O$, in the presence of a base, preferably N,N-diisopropylethylamine, in an inert chlorocarbon solvent, preferably dichloromethane, at a temperature between about 20 and about 50° C., followed by treatment with an alkali metal alkoxide, preferably sodium methoxide, in an alcoholic solvent, preferably methanol, at a temperature between about 20 and about 50° C., and optionally thereafter removing any protecting groups.

Compounds of formulae (II), (XVII), and (XVIII) form a further aspect of the invention.

Salts of the compounds of formula (I) may be formed by reacting the free base, or a salt or a derivative thereof, with one or more equivalents of the appropriate acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$ ($P2Y_{ADP}$ or $P2T_{AC}$) receptor antagonists. Accordingly, the compounds are useful in therapy, including combination therapy, particularly they are indicated for use as: inhibitors of platelet activation, aggregation and degranulation, promoters of platelet disaggregation, anti-thrombotic agents or in the treatment or prophylaxis of unstable angina, coronary revascularisation procedures including angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, antiphospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to the invention there is further provided the use of a compound according to the invention as an active ingredient in the manufacture of a medicament for use in the treatment or prevention of the above disorders. In particular the compounds of the invention are useful for treating myocardial infarction, thrombotic stroke, transient ischaemic attacks, peripheral vascular disease and stable and unstable angina, especially unstable angina. The invention also provides a method of treatment or prevention of the above disorders which comprises administering to a person suffering from or susceptible to such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres, which break up during the inhalation procedure. This spheronized powder may be filled into the drug reservoir of a multidose inhaler, e.g. that known as the Turbuhaler® in which a dosing unit meters the desired dose which is then inhaled by the person. With this system the active compound with or without a carrier substance is delivered to the person.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution, which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

EXAMPLES

The invention is illustrated by the following non-limiting examples.

In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer.

Preparative HPLC separations were generally performed using a Novapak®, Bondapak® or Hypersil® column packed with BDSC-18 reverse phase silica. Flash chromatography (indicated in the Examples as (SiO$_2$)) was carried out using Fisher Matrix silica, 35–70 μm. For examples which showed the presence of rotamers in the proton NMR spectra only the chemical shifts of the major rotamer are quoted.

Example 1

[1S-[1α,2α,3β,5β(1S*, 2R*)]]-3-(2-Hydroxyethoxy)-5-[7-[N-methyl-(2-phenylcyclopropyl)amino]-5-(propylthio)-3H-[1,2,3]-triazolo[4,5-d]pyrimidin-3-yl]cyclopentane-1,2-diol a) (1R-cis)-bis(1,1-Dimethylethyl)-4-hydroxy-2-cyclopentenylimidodicarbonate Imidodicarbonic acid bis-(1,1-dimethylethyl) ester (25.0 g) was added to a suspension of ether-washed sodium hydride (3.94 g of a 60% dispersion in oil) in tetrahydrofuran (500 ml). The mixture was stirred at 50° C. for 2 hours. (1S-cis)-4-acetoxy-2-cyclopenten-1-ol (10.0 g) and tetrakis(triphenylphosphine)palladium (0) (2.0 g) was added to the reaction mixture, at ambient temperature. The reaction mixture was stirred for 24 hours diluted with water and extracted with ethyl acetate. The organic extracts were dried, concentrated in vacuo and the residue purified by chromatography (SiO$_2$, ethyl acetate: hexane 1:5 as eluant) to give the sub-title compound as a solid (20.0 g).

NMR δ H (d$_6$-DMSO) 5.71–5.77 (2H, m), 4.91 (1H, d, J=5.4 Hz), 4.86 (1H, tq, J=8.0, 1.8), 4.51–4.57 (1H, m), Hz), 2.54 (1H, dt, J=12.6, 7.4 Hz), 1.61 (1H, ddd, J=12.3, 7.7, 6.4 Hz), 1.43 (18H, s).

b) [1R-(1α,2β,3β,4α)]-2,3,4-Trihydroxycyclopentenylimidodicarbonic Acid, bis(1,1-dimethylethyl) Ester N-methylmorpholine-N-oxide (11.08 g) was added to a solution of the product of step a) (20.0 g) in tetrahydrofuran (500 ml) and water (50 ml). Subsequently osmium tetroxide (11.75 ml, 2.5% solution in t-butanol) was added and the mixture was stirred at room temperature overnight then treated with sodium hydrosulphite (6.0 g). The suspension was filtered through Celite and the solid residue washed with methanol. The filtrate was concentrated in vacuo and the residue purified by chromatography (SiO$_2$, ethyl acetate: hexane 1:1 as eluant) to afford the sub-title compound (17.37 g).

NMR δ H (d$_6$-DMSO) 4.82 (1H, d, J=4.6 Hz), 4.56 (1H, d, J=5.9 Hz), 4.54 (1H, d, J=4.8 Hz), 4.11–4.21 (2H, m), 3.66–3.73 (1H, m), 3.55–3.58 (1H, m), 1.97–2.05 (1H, m), 1.46–1.60 (1H, m), 1.44 (18H, s).

c) [3aR-(3aα,4α,6α,6aα)]-6-Amino-2,2-dimethyl-tetrahydro-4H-cyclopenta-1,3-dioxol-4-ol p-Toluenesulphonic acid (0.86 g) was added to a solution of the product of step b) (15.0 g) in acetone (250 ml) containing 2,2-dimethoxypropane (22.1 ml). The mixture was stirred at ambient temperature for 30 minutes. The mixture was partitioned between ethyl acetate (700 ml) and brine (300 ml) and the organic extracts were dried (MgSO$_4$) and concentrated in vacuo. Water (250 ml) was added water to the residual gum and the mixture heated at reflux for 24 hours. The cooled reaction mixture was concentrated in vacuo and dried by azeotropic distillation with toluene to provide sub-title compound (7.5 g).

MS (APCI) 174 (M+H$^+$, 100%).

d) [3aR-(3aα,4α,6α,6aα)]-6-[[6-Chloro-5-nitro-2-(propylthio)-pyrimidin-4-yl]amino]-2,2-dimethyl-tetrahydro-4H-cyclopenta-1,3-dioxol-4-ol A solution of the product of step c) (7.5 g) in tetrahydrofuran (500 ml) was added over 1 hour to a solution of 4,6-dichloro-5-nitro-2-(propylthio)pyrimidine (prepared as described in International Patent Application WO 9703084) (25.57 g) and N,N-diisopropylethylamine (8.3 ml) in tetrahydrofuran (1000 ml) and stirred for a further 1 hour. The reaction mixture was concentrated in vacuo, ethyl acetate added (1000 ml) and the mixture was washed with water. The organic layer was dried (MgSO$_4$), evaporated and the residue purified by chromatography (SiO$_2$, isohexane-ethyl acetate as eluant) to afford the sub-title compound (14.22 g).

MS (APCI) 405/7 (M+H$^+$), 405 (100%).

e) [3aR-(3aα,4α,6α,6aα)]-6-[[5-Amino-6-chloro-2-propylthiopyrimidin-4-yl]amino]-2,2-dimethyl-tetrahydro-4H-cyclopenta-1,3-dioxol-4-ol Iron powder (15.0 g) was added to a stirred solution of the product of step d) (13.45 g) in acetic acid (500 ml). The reaction mixture was stirred at room temperature for 2 hours and concentrated to half volume in vacuo. The residue was diluted with ethyl acetate and the mixture washed with water. The organic layer was dried (MgSO$_4$) and concentrated in vacuo to afford the sub-title compound (10.26 g).

MS (APCI) 375/7 (M+H$^+$), 375 (100%).

f) [3aR-(3aα,4α,6α,6aα)]-6-[7-Chloro-5-(propylthio)-3H-[1,2,3]-triazolo[4,5-d]-pyrimidin-3-yl]-2,2-dimethyl-tetrahydro-4H-cyclopenta-1,3-dioxol-4-ol Isoamyl nitrite (5.5 ml) was added to a solution of the product of step e) (10.26 g) in acetonitrile (500 ml) and the solution heated at 70° C. for 1 hour. The cooled reaction mixture was concentrated in vacuo and the residue purified by chromatography (SiO$_2$, ethyl acetate:isohexane 2:1 as eluant) to afford the sub-title compound (8.93 g).

MS (APCI) 386/8 (M+H$^+$), 386 (100%).

g) [3aR-[3aα,4α,6α(1R*, 2S*),6aα]]-Tetrahydro-2,2-dimethyl-6-[7-[N-methyl-(2-phenylcyclopropyl)amino]-5-(propylthio)-3H-[1,2,3]-triazolo[4,5-d]pyrimidin-3-yl]-4H-cyclopenta-1,3-dioxol-4-ol A mixture of the product of step f) (1.0 g), (1R-trans)-N-methyl-2-phenylcyclopropanamine hydrochloride (prepared as described by C. Kaiser et al, J. Org. Chem., 1962, 27, 768–773, using (1R-trans)-2-phenylcyclopropanamine, [R-(R*,R*)]-2,3-dihydroxybutanedioate (1:1) (prepared as described by L. A. Mitscher et al, J. Med. Chem., 1986, 29, 2044) (0.522 g) and N,N-diisopropylethylamine (1.35 ml) in ether (20 ml) was stirred at room temperature for 2 hours. The reaction mixture was washed successively with 1 M hydrochloric acid, saturated aqueous sodium bicarbonate solution and brine, dried (MgSO$_4$) and concentrated in vacuo to afford the sub-title compound (1.23 g).

MS (APCI) 497 (M+H$^+$, 100%).

h) [3aS-[3aα,4α(1S*,2R*),6α,6aα]-N-Methyl-N-(2-phenylcyclopropyl)-3-[[[[(tetrahydro-2H-pyran-2-yl)oxy]ethyl]oxy]-2,2-dimethyl-4H-cyclopenta-1,3-dioxol-4-yl]-5-(propylthio)-3H-[1,2,3]-triazolo[4,5-d]pyrimidin-7-amine.

Aqueous NaOH (5N, 10 ml) was added to a solution of the product of step g) (1.23 g) in toluene (10 ml). Subsequently, tetrabutylammonium bromide (0.12 g) was added and the mixture stirred for 30 minutes. Dimethyl sulfoxide (704 μl) and 2-(2-bromoethoxy)-2H-tetrahydropyran (3.93 ml) were added and the reaction mixture was heated at reflux for 16 hours. Further 2-(2-bromoethoxy)-2H-tetrahydropyran (3.93 ml) and tetrabutylammonium bromide (0.12 g) were added and the reaction mixture was heated at reflux for 16 hours. The reaction mixture was washed with water and brine, dried (MgSO$_4$) and concentrated in vacuo. The resi due was purified by chromatography (SiO$_2$, ethyl acetate: hexane 1:4 as eluant) to afford the sub-title compound (1.2 g).

MS (APCI) 625 (M+H$^+$, 100%).

i) [1S-[1α,2α,3β,5β(1S*, 2R*)]]-3-(2-Hydroxyethoxy)-5-[7-[N-methyl(2-phenylcyclopropyl)amino]-5-(propylthio)-3H-[1,2,3]-triazolo[4,5-d]pyrimidin-3-yl]cyclopentane-1,2-diol A solution of the product of step h) (0.50 g) in trifluoroacetic acid (9 ml) and water (1 ml) was stirred at room temperature for 1 hour then concentrated in vacuo and the residue purified by chromatography (HPLC, Novapak® C18 column, 0.1% aqueous ammonium acetate:acetonitrile, 55:45) to afford the title compound (0.113 g).

MS (APCI) 501 (M+H$^+$, 100%).

NMR δ H (d$_6$-DMSO) 7.31–6.87 (5H, m), 4.98 (1H, q, J=8.5 Hz), 4.81 (1H, d, J=6.5 Hz), 4.73 (1H, d, J=4.1 Hz), 4.61–4.56 (1H, m), 4.29 (1H, br s), 4.00–3.97 (1H, m), 3.83–3.79 (1H, m), 3.56–3.49 (7H, m), 3.08–3.01 (2H, m), 2.98–2.91 (1H, m), 2.66–2.58 (1H, m), 2.41 (1H, m), 2.10–2.03 (1H, m), 1.63 (1H, sextet, J=7.2 Hz), 1.58–1.53 (1H, m), 1.45 (1H, q, J=6.6 Hz), 0.94 (3H, t, J=7.2 Hz).

Example 2

[1S-[1α,2β,3β,4α(1S*, 2R*)]]-4-[7-[N-Methyl-(2-phenylcyclopropyl)amino]-5-(propylthio)-3H-[1,2,3]-triazolo[4,5-d]pyrimidin-3-yl]cyclopentane-1,2,3-triol a) [1S-(1α,2β,3β,4α)]-[4-[6-Chloro-5-nitro-2-(propylthio)pyrimidin-4-yl]amino]cyclopentane-1,2,3-triol 2M hydrochloric acid (5 ml) was added to a solution of the product of Example 1, step b) (0.6 g) in methanol (10 ml). The mixture was stirred for 24 hours, concentrated in vacuo and dried by azeotropic distillation with toluene. A solution of 4,6-dichloro-5-nitro-2-(propylthio)-pyrimidine (prepared as described in International Patent Application WO 9703084) (0.82 g) in tetrahydrofuran (5 ml) was added to a suspension of the residual amine hydrochloride and N,N-diisopropylethylamine (1.78 ml) in tetrahydrofuran (10 ml). The mixture was heated at reflux for 24 hours, cooled, concentrated in vacuo and the residue purified by chromatography (SiO$_2$, isohexane-ethyl acetate 3:7 as eluant) to afford the sub-title compound (0.469 g).

MS (APCI) 365n (M+H$^+$), 365 (100%).

b) [1S-(1α,2β,3β,4α)]-[4-[5-Amino-6-chloro-2-(propylthio)pyrimidin-4-yl]amino]cyclopentane-1,2,3-triol The sub-title compound was prepared according to the method of Example 1, step e) using the product of step a) and was used directly in the next step.

c) [1S-(1α,2β,3β,4α)]4-[7-Chloro-5-(propylthio)-3H-[1,2,3]-triazolo[4,5-d]pyrimidin-3-yl]cyclopentane-1,2,3-triol The sub-title compound was prepared according to the method of Example 1, step f) using the product of step b).

MS (APCI) 346/8 (M+H$^+$), 346 (100%).

d) [1S-[1α,2β,3β,4α(1S*,2R*)]]4-[7-[(2-Phenylcyclopropyl)amino]-5-(propylthio)-3H-[1,2,3]-triazolo[4,5-d]pyrimidin-3-yl]cyclopentane-1,2,3-triol The sub-title compound was prepared according to the method of Example 1, step g) using the product of step c) and (1R-trans)-2-phenylcyclopropanamine, [R-(R*,R*)]-2,3-dihydroxybutanedioate (1:1) (prepared as described by L. A. Mitscher et al, J. Med. Chem., 1986, 29, 2044).

MS (APCI) 443 (M+H$^+$,100%).

e) [1R-[1α(1R*,2S*),2β,3β,4α]]-N-(2-Phenylcyclopropyl)-5-(propylthio)-3-[2,3,4-tris[[(1,1-dimethylethyl)dimethylsilyl]oxy]cyclopentyl]-3H-[1,2,3]-triazolo[4,5-d]pyrimidin-7-amine A mixture of the product of step d) (1.79 g), tert-butyldimethylsilylchloride (1.22 g) and imidazole (1.10 g) in N,N-dimethylformamide (3 ml) was stirred at ambient temperature for 24 hours. Further tert-butyldimethylsilylchloride (1.0 g) was added and the mixture stirred for a further 6 hours. The reaction mixture was concentrated in vacuo and the residue purified by chromatography (SiO$_2$, ethyl acetate: hexane 1:20 as eluant) to afford the sub-title compound (2.43 g).

NMR δH (CDCl$_3$) 7.34–7.18 (5H, m), 6.38 and 3.22 (1H, br s), 5.30–5.19 (1H, m), 4.96–4.89 (1H, m), 4.04–3.99 (1H, m), 3.89–3.86 (1H, m), 3.11–3.01 (2H, m), 2.83–2.70 (1H, m), 2.24–2.16 (1H, m), 2.14–2.03 (1H, m), 1.75–1.61 (2H, m), 1.5–1.3 (2H, m), 0.98–0.92 (3H, m), 0.94 (9H, s), 0.93 (9H, s), 0.69 (9H, s), 0.13 (3H, s), 0.12 (3H, s), 0.09 (3H, s), 0.08 (3H, s), −0.19 (3H, s), −0.47 (3H, s).

f) [1R-[1α(1R*,2S*),2β,3β,4α]]-N-Methyl-N-(2-phenylcyclopropyl)-5-(propylthio)-3-[2,3,4-tris[[(1,1-dimethylethyl)dimethylsilyl]oxy]cyclopentyl]-3H-[1,2,3)-triazolo[4,5-d]pyrimidin-7-amine Sodium hydride (35 mg of a 60% dispersion in oil) was added to a solution of the product of step e) (0.576 g) in tetrahydrofuran (10 ml). The solution was stirred at ambient temperature for 30 minutes and methyl iodide (68 μl) was added. After 5 hours further methyl iodide (68 μl) was added and stirring was continued for 36 hours. The reaction mixture was concentrated in vacuo and the residue purified by chromatography (SiO$_2$, ethyl acetate: hexane 1:20 as eluant) to afford the sub-title compound (0.537 g).

NMR δ H (CDCl$_3$) 7.35–7.18 (5H, m), 5.32–5.22 (1H, m), 4.89 (1 H, dd, J=8.3, 3.3 Hz), 4.03 (1H, dt, J=6.5, 1.7 Hz), 3.91–3.87 (1H, m), 4.4–3.6 (3H, br s), 3.12–3.02 (2H, m), 2.82–2.70 (1H, m), 2.38–2.26 (1H, m), 2.17–2.05 (1H, m), 1.80–1.65 (2H, m), 1.48–1.40 (1H, m), 1.27–0.65 (5H, m), 0.95 (9H, s), 0.93 (9H, s), 0.69 (9H, s), 0.13 (3H, s), 0.12 (3H, s), 0.09 (3H, s). 0.08 (3H, s), −0.19 (3H, s), −0.45 (3H, s).

g) [1S-[1α,2β,3β,4α(1S*,2R*)]]-4-[7-[N-methyl-(2-phenylcyclopropyl)amino]-5-(propylthio)-3H-[1,2,3]-triazolo[4,5-d]pyrimidin-3-yl]cyclopentane-1,2,3-triol Tetrabutylammonium fluoride (1M in tetrahydrofuran/water 95/5; 2.3 ml) was added to a solution of the product of step f) (0.53 g) in tetrahydrofuran (10 ml). The solution was stirred at ambient temperature for 20 hours, concentrated in vacuo and the residue purified by chromatography (HPLC, Novapak® C18 column, 0.1% aqueous ammonium acetate:acetonitrile) to afford the title compound (0.23 g).

MS (APCI) 457 (M+H$^+$, 100%).

NMR δ H (d$_6$-DMSO) 7.32–7.18 (5H, m), 4.97 (1H, q, J=8.5 Hz), 4.91 (1H, d, J=4.5 Hz), 4.77 (1H, d, J=6.5 Hz), 4.68–4.63 (2H, m), 3.97–3.95 (1H, m), 3.82 (1H, m), 3.57 (3H, br s), 3.15–2.90 (3H, m), 2.63–2.33 (2H, m), 1.97–1.93 (1H, m), 1.63–1.54 (3H, m), 1.45–143 (1H, m), 0.93 (3H, t, J=7.0 Hz).

Example 3

[1S-1α,2α,3β,5β(1S*,2R*)]]-3-(Hydroxymethyl)-5-[7-[N-methyl-2-phenylcyclopropyl)amino]-5-(propylthio)-3H-[1,2,3]-triazolo[4,5-d]pyrimidin-3-yl]cyclopentane-1,2-diol a) [3aR-[3aα,4α,6α(1R*,2S*),6aα]-Tetrahydro-2,2-dimethyl-6-[7-[N-methyl-(2-phenylcyclopropyl)amino]-5-(propylthio)-3H-[1,2,3]-triazolo[4,5-d]pyrimidin-3-yl]-4H-cyclopenta-1,3-dioxole-4-methanol N,N-Diisopropylethylamine (2 ml) was added to a solution of [3aR-(3aα,4α,6α,6aα)][7-chloro-5-(propylthio)-3H-[1,2,3]-triazolo[4,5-d]pyrimidin-3-yl]-tetrahydro-2,2- dimethyl-4H-cyclopenta-1,3-dioxole-4-methanol (prepared as described in International Patent Application WO 9703084) (1.15 g) and (1R-trans)-N-methyl-2-phenylcyclopropanamine hydrochloride (prepared as described by C. Kaiser et al, J. Org. Chem., 1962, 27, 768–773, using (1R-trans)-2-phenylcyclopropanamine, [R-(R*,R*)]-2,3-dihydroxybutanedioate (1:1) (prepared as described by L. A. Mitscher et al, J. Med. Chem., 1986, 29, 2044)) (0.53 g) in dichloromethane (20 ml). The reaction mixture was stirred at room temperature for 18 hours, then washed with water, dried and concentrated in vacuo. The residue was purified by chromatography (SiO$_2$, ethyl acetate:isohexane 1:1 as eluent) to afford the sub-title compound (1.3 g).

MS (APCI) 511 (M+H$^+$, 100%).

b) [1S-[1α,2α,3β,5β(1S*,2R*)]]-3-(Hydroxymethyl)-5-[7-[N-methyl-(2-phenylcyclopropyl)amino]-5-(propylthio)-3H-[1,2,3]-triazolo[4,5-d]pyrimidin-3-yl]cyclopentane-1,2-diol A solution of the product from step a) (0.25 g) in methanol (8 ml) and 2N HCl (2 ml) was stirred at room temperature for 3 hours and then concentrated in vacuo. The residue was triturated with acetonitrile (5 ml) to yield a white solid which was collected by filtration. Trituration with methanol (5 ml) afforded the title compound (0.19 g).

MS (APCI) 471 (M+H$^+$, 100%).

NMR δ H (d$_6$-DMSO at 90° C.) 7.33–7.20 (5H, m), 5.02 (1H, q), 4.46 (1H, q), 3.93 (1H, q), 3.59–3.46 (5H, m), 3.08–2.98 (3H, m), 2.44–2.40 (1H, m), 2.31–2.24 (1H, m), 2.18–2.12 (1H, m), 1.92–1.85 (1H, m), 1.68–1.53 (3H, m), 1.44 (1H, q), 0.95 (3H, t).

Example 4

[1S-[1α,2β,3β,4α(1S*,2R*)]]-4-[7-[N-[2-(3,4-Difuorophenyl)cyclopropyl]-N-methylamino]-5-(propylthio)-3H-[1,2,3]-triazolo[4,5-d]pyrimidin-3-yl]cyclopentane-1,2,3-triol a) (1R-trans)-N-[2-(3,4-Difluorophenyl)cyclopropyl] acetamide Acetic anhydride (0.31 ml) was added to a suspension of (1R-trans)-2-(3,4-difluorophenyl)cyclopropanamine, (R-(R*,R*)]-2,3-dihydroxybutanedioate (1:1) (prepared as described in International Patent Application WO 9905143) (700 mg) and potassium carbonate (1.0 g) in tetrahydrofuran (20 ml) and stirred for 20 h. Saturated ammonium chloride solution was added and the mixture was extracted with ether and the organic layers were dried (MgSO$_4$) and evaporated to afford the sub-title compound (470 mg).

MS (APCI) 270 (M+MeCO$_2$, 100%).

b) (1R-trans)-N-[2-(3,4-Difluorophenyl)cyclopropyl]-N-methylacetamide

Sodium hydride (109 mg of a 60% dispersion in oil) was added to a solution of the product from step a) (470 mg) and methyl iodide (0.4 ml) in tetrahydrofuran (15 ml) and stirred for 18 h. Saturated ammonium chloride solution was added and the mixture was extracted with ether. The organic layers were dried (MgSO$_4$), evaporated and purified by chromatography (SiO$_2$, dichloromethane:methanol (49:1) as eluent) to give the sub-title compound (470 mg).

MS (APCI) 226 (M+H$^+$, 100%).

c) (1R-trans)-2-(3,4-Difluorophenyl)-N-methylcyclopropanamine, Hydrochloride

A solution of the product from step b) (443 mg) in 4M HCl (10 ml) was refluxed for 8 h. The solvent was removed in vacuo to give the sub-title compound (357 mg).

NMR δ H (d$_6$-DMSO) 9.25 (1H, s), 7.39–7.30 (2H, m), 7.09–7.02 (1H, m), 2.98–2.95 (1H, m), 2.64 (3H, s), 1.52–1.51 (1H, m), 1.31–1.29 (2H, m).

d) [3aR-[3aα,4α,6α(1R*,2S*),6aα]-Tetrahydro-2,2-dimethyl-6-[7-[N-[2-(3,4-difluorophenyl)cyclopropyl]-N-methylamino]-5-(propylthio)-3H-[1,2,3]-triazolo[4,5-d]pyrimidin-3-yl]-4H-cyclopenta-1,3-dioxole-4-ol The sub-title compound (800 mg) was prepared according to the method of Example 3, step a) from the product of Example 1, step f) (612 mg) and the product from step c) (357 mg).

MS (APCI) 533 (M+H$^+$, 100%).

e) [1S-[1α,2β,3β,4α(1S*, 2R*)]]4-[7-[N-[2-(3,4-Difluorophenyl)cyclopropyl]-N-methylamino]-5-(propylthio)-3H-[1,2,3]-triazolo[4,5-d]pyrimidin-3-yl]cyclopentane-1,2,3-triol A solution of the product from step a) (798 mg) in a mixture of trifluoroacetic acid (8 ml), methanol (5 ml) and water (3 ml) was stirred at room temperature for 1 hour, poured into 2M potassium carbonate and extracted with ethyl acetate. The extract was concentrated in vacuo and the residue purified by chromatography (SiO$_2$, dichloromethane:methanol (14:1) as eluant) to afford the title compound (703 mg).

MS (APCI) 493 (M+H$^+$, 100%).

NMR δ H (d$_6$-DMSO) 7.40–7.30 (2H, m), 7.15–7.03 (1H, m), 5.12 (1H, dd), 5.03–4.95 (2H, m), 4.93 (1H, d), 4.68 (1H, q), 3.98–3.55 (3H, m), 3.10–2.90 (1H, m), 2.85–2.72 (1H, m), 2.64–2.54 (1H, m), 2.40–2.20 (1H, m), 1.97–1.85 (1H, m), 1.80–1.42 (4H, m), 1.02–0.82 (3H, m).

Example 5

[1S-[1α,2β,3β,4α(1S*,2R*)]]4-[7-N-[2-(4-Methoxyphenyl)cyclopropyl]-N-methylamino]-5-(propylthio)-3H-[1,2,3]-triazolo[4,5-d]pyrimidin-3-yl]cyclopentane-1,2,3-triol a) (1R-trans)-N-[2-(4-Methoxyphenyl)cyclopropyl] acetamide The sub-title compound was prepared according to the method of Example 4, step a) from (1R-trans)-2-(4-methoxyphenyl)cyclopropanamine, [R-(R*,R*)]-2,3-dihydroxybutanedioate (1:1) (prepared as described in WO9905143) to give a white solid (655 mg).

MS (APCI) 206 (M+H$^+$, 100%).

b) (1R-trans)-N-[2-(4-Methoxyphenyl)cyclopropyl]-N-methylacetamide

The sub-title compound was prepared according to the method of Example 4, step b) using the product from step a) to afford a white solid (587 mg).

MS (APCI) 220 (M+H$^+$, 100%).

c) (1R-trans)-2-(4-Methoxyphenyl)-N-methylcyclopropanamine, Hydrochloride

The sub-title compound was prepared according to method of Example 4, step c) from the product of step b) to afford a white solid (507 mg).

NMR δ H (d$_6$-DMSO) 9.24 (2H, s), 7.11–7.09 (2H, m), 6.87–6.85 (2H, m), 3.72 (3H, s), 2.88–2.84 (1H, m), 2.64 (3H, s), 2.44–2.39 (1H, m), 1.46–1.41 (1H, m), 1.97–1.15 (1H, m).

d) [1S-[1α,2β,3β,4α(1S*,2R*)]]4-[7-N-[2-(4-Methoxyphenyl)cyclopropyl]-N-methylamino]-5-(propylthio)-3H-[1,2,3]-triazolo[4,5-d]pyrimidin-3-yl]cyclopentane-1,2,3-triol The title compound (400 mg) was prepared according to the method of Example 3, step a) from the product of Example 1, step f) (765 mg) and the product from step c) (507 mg), followed by deprotection using the method of Example 4, step e).

MS (APCI) 487 (M+H+, 100%).

NMR δ H (d$_6$-DMSO) 7.20–7.17 (2H, m), 6.88–6.85 (2H, m), 4.98–4.96 (1H, q), 4.69–4.65 (1H, m), 3.98–3.97 (1H, m), 3.85–3.82 (1H, m), 3.74 (3H, s), 3.56 (3H, s), 3.55–3.41 (4H, m), 3.07–2.99 (2H, m), 2.50–2.48 (1H, m), 2.47–2.38 (1H, m), 2.00–1.96 (1H, m), 1.68–1.61 (2H, m), 1.50–1.47 (1H, m), 1.38–1.36 (1H, m), 0.97–0.92 (3H, t).

Example 6

[1S-[1α,2α,3β,5β(1S*,2R*)]]-3-Azidomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol a) [3aR-[3aα,4α,6α(1R*,2S*),6aα]]-N-Methyl-N-(2-phenylcyclopropyl)-5-(propylthio)-3-[tetrahydro-6-(iodomethyl)-2,2-dimethyl-3aH-cyclopenta[d][1,3]dioxol-4-yl]-3H-[1,2,3]-triazolo[4,5-d]pyrimidin-7-amine A solution of the product from Example 3a) (1.0 g) in dichloromethane (10 ml) was treated with methyltriphenoxyphosphonium iodide (1.5 g) and the resultant solution was left to stand for 30 minutes at room temperature. This mixture was then purified by chromatography (SiO$_2$, ethyl acetate:isohexane 1:4 as eluant) to afford the sub-title compound (0.77 g).

MS (APCI) 621 (M+H+, 100%).

b) [1S-[1α,2α,3β,5β(1S*7R*)]]-3-Iodomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol A solution of the product from step a) (0.76 g) in a mixture of tetrahydrofuran (6 ml) and methanol (4 ml) was treated with 2 molar aqueous hydrochloric acid (1.5 ml) and the solution allowed to stand at 35° C. for 5 hours. The mixture was concentrated in vacuo and the residue was azeotroped with toluene (3×100 ml). The residue was purified by chromatography (SiO$_2$, ethyl acetate:isohexane 1:2 as eluant) to afford the sub-title compound (0.53 g).

MS (APCI) 581 (M+H+, 100%).

c) [1S-[1α,2α,3β,5β(1S*,2R*)]]-3-Azidomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol A solution of the product from step b) (0.53 g) in dimethyl sulphoxide (5 ml) was treated with sodium azide (0.07 g) and the resultant mixture was stirred at room temperature for ~18 hours. The mixture was partitioned between ethyl acetate (200 ml) and a saturated solution of aqueous brine (200 ml). The ethyl acetate layer was washed with water (3×100 ml), dried (MSO$_4$) and concentrated in vacuo to afford the title compound (0.43 g).

MS (APCI) 496 (M+H+, 100%).

NMR δ H (d$_6$:DMSO) 7.32–7.19 (5H, m), 5.01 (1H, q), 4.81 (1H, d), 4.63 (1H, d), 4.41 (1H, q), 3.91 (1H, q), 3.60–3.49 (2H, m), 3.06–2.98 (6H, m), 2.45–2.35 (2H, m), 2.30–2.20 (1H, m), 1.91–1.86 (1H, m), 1.67–1.52 (3H, m), 1.45–1.42 (1H, m), 0.94 (3H, t).

Example 7

[1S-[1α,2α,3β,5β(1S*,2R*)]]-3-Aminomethyl-5-[7-[N-methyl-(2-phenylcyclopropyl)amino]-5-(propylthio)-3H-[1,2,3]-triazolo[4,5-d]pyrimidin-3-yl]cyclopentane-1,2-diol, Hydrochloride Salt A solution of the product from Example 6, step c) (0.39 g) in ethanol (15 ml) was treated with 10% palladium on carbon catalyst (0.04 g) and the resultant mixture was stirred vigorously under 4 atmospheres of hydrogen for 4 hours. The catalyst was removed by filtration and the filtrate concentrated in vacuo. The residue was dissolved in 1,4-dioxane (10 ml) and then treated with a slight excess of concentrated hydrochloric acid. The solution was concentrated in vacuo and the residue azeotroped with toluene (3×100 ml) before being triturated with ethyl acetate to afford the title compound (0.16 g).

MS (APCI) 470 (M+H+, 100%).

NMR δ H (d$_6$-DMSO at 90° C.) 8.00 (3H, s), 7.33–7.17 (5H, m), 5.03–4.96 (1H, m), 4.37 (1H, t), 4.01 (1H, t), 3.56 (3H, s), 3.10–2.93 (4H, m), 2.45–2.35 (2H, m), 1.90–1.79 (1H, m), 1.67–1.53 (3H, m), 1.44 (1H, q), 0.94 (3H, t).

Example 8

[1R-[1α,2β,3β,4α(1R*,2S*)]]-N-[2,3-Dihydroxy-4-[7-[N-methyl-(2-phenylcyclopropyl)amino]-5-(propylthio)-3H-[1,2,3]-triazolo[4,5-d]pyrimidin-3-yl]cyclopentylmethyl]acetamide A solution of the product from Example 7 (0.2 g) in dichloromethane (15 ml) was treated with N,N-diisopropylethylamine (0.11 g) followed by acetic anhydride (0.16 g) and the resultant mixture was stirred at room temperature for 4 hours. The mixture was washed with a saturated solution of aqueous sodium bicarbonate (15 ml) and the organic layer concentrated in vacuo. The residue was dissolved in a 0.1 molar solution of sodium methoxide in methanol (20 ml) and the solution allowed to stand for 2 hours at room temperature. Following concentration in vacuo the residue was acidified by careful addition of acetic acid, the mixture was again concentrated in vacuo and he residue azeotroped with toluene (3×100 ml). Purification by chromatography (SiO$_2$ methanol:chloroform 1:24 as eluant) gave the title compound (0.12 g).

MS (APCI) 512.5 (M+H+, 100%).

NMR δ H (d$_6$-DMSO at 90° C.) 7.63 (1H, s), 7.32–7.19 (5H, m), 4.98 (1H, q), 4.72 (1H, d), 4.48–4.44 (2H, m), 3.86 (1H, q), 3.34–3.29 (1H, m), 3.12–3.06 (1H, m), 3.05–2.97 (5H, m), 2.42–2.39 (1H, m), 2.37–2.30 (1H, m), 2.20–2.15 (1H, m), 1.81–1.75 (4H, m), 1.67–1.52 (3H, m), 1.44 (1H, q), 0.94 (3H, t).

Pharmacological Data

The preparation for the assay of the P$_{2T}$ (P2Y$_{ADP}$ or P2T$_{AC}$) receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240G to obtain a platelet-rich plasma (PRP) to which 300 ng/ml prostacyclin was added to stabilize the platelets during the washing procedure. Red cell free PRP was obtained by centrifugation for 10 minutes at 125G followed by further centrifugation for 15 minutes at 640G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows

Aggregation responses in 96 well plates were measured using the change in absorbance given by the plate reader at 660 nm. Either a Bio-Tec Ceres 900C or a Dynatech MRX was used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an IC$_{50}$. Compounds exemplified have pIC$_{50}$ values of more than 5.0.

What is claimed is:

1. A compound of formula (I):

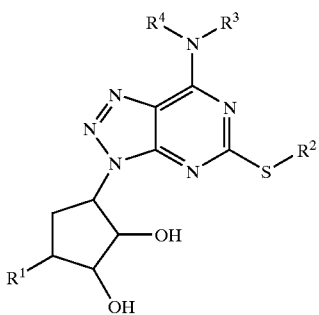

wherein:
R$^1$ is OR$^5$ or CH$_2$R$^6$;
R$^2$ is alkyl C$_{1-6}$ or haloalkyl C$_{1-6}$;
R$^3$ is cycloalkyl C$_{3-6}$, optionally substituted by R$^7$;
R$^4$ is alkyl C$_{1-6}$;
R$^5$ is H or alkyl C$_{1-6}$, optionally substituted by OH;
R$^6$ is OH, N$_3$, or NHR$^8$;
R$^7$ is phenyl, optionally substituted by one or more groups selected from alkyl C$_{1-6}$, halogen, and OR$^{10}$;
R$^8$ is H, alkyl C$_{1-6}$, or COR$^9$;
R$^9$ is alkyl C$_{1-6}$;
R$^{10}$ is alkyl C$_{1-6}$;
or a pharmaceutically acceptable salt or solvate thereof, or a solvate of such a salt.

2. A compound according to claim 1 which is:

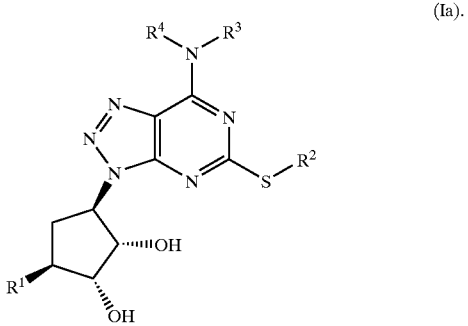

3. A compound according to claim 2 in which R$^3$ is

4. A compound according to claim 1, in which R$^1$ is OH, O(CH$_2$)$_2$OH, CH$_2$OH, CH$_2$N$_3$, CH$_2$NH$_2$ or CH$_2$NHAc.

5. A compound according to claim 1, in which R$^2$ is n-Pr.

6. A compound according to claim 1, in which R$^3$ is cyclopropyl optionally substituted with phenyl.

7. A compound according to claim 6 in which R$^3$ is cyclopropyl substituted with phenyl, optionally substituted by one or more groups selected from alkyl C$_{1-6}$, halogen and OR$^{10}$.

8. A compound according to claim 1 in which R$^4$ is methyl.

9. A compound according to claim 1 which is:
[1S-[1α,2α,3β,5β(1S*,2R*)]]3-(2-Hydroxyethoxy)-5-[7-[N-methyl-(2-phenylcyclopropyl)amino]-5-(propylthio)-3H-[1,2,3]-triazolo[4,5-d]pyrimidin-3-yl] cyclopentane-1,2-diol; [1S-[1α,2β,3β,4α(1S*,2R*)]]-4-[7-[N-methyl-(2-phenylcyclopropyl)amino]-5-(propylthio)-3H-[1,2,3]-triazolo[4,5-d]pyrimidin-3-yl] cyclopentane-1,2,3-triol;

[1S-[1α,2α,3β,5β(1S*,2R*)]]-3-(Hydroxymethyl)-5-[7-[N-methyl-(2-phenylcyclopropyl)amino]-5-(propylthio)-3H-[1,2,3]-triazolo[4,5-d]pyrimidin-3-yl] cyclopentane-1,2-diol;

[1S-[1α,2β,3β,4α(1S*,2R*)]]-4-[7-[N-[2-(3,4-Difluorophenyl)cyclopropyl]-N-methylamino]-5-(propylthio)-3H-[1,2,3]-triazolo[4,5-d]pyrimidin-3-yl] cyclopentane-1,2,3-triol;

[S-[1α,2β,3β,4α(1S*,2R*)]]-4-[7-[N-[2-(4-Methoxyphenyl)cyclopropyl]-N-methylamino]-5-(propylthio)-3H-[1,2,3]-triazolo[4,5-d]pyrimidin-3-yl] cyclopentane-1,2,3-triol;

[1S-[1α,2α,3β,5β(1S*,2R*)]]-3-Azidomethyl-5-[7-[N-methyl-(2-phenylcyclopropyl)amino]-5-(propylthio)-3H-[1,2,3]-triazolo[4,5-d]pyrimidin-3-yl] cyclopentane-1,2-diol;

[1S-[1α,2α,3β,5β(1S*,2R*)]]-3-Aminomethyl-5-[7-[N-methyl-(2-phenylcyclopropyl)amino]-5-(propylthio)-3H-[1,2,3]-triazolo[4,5-d]pyrimidin-3-yl] cyclopentane-1,2-diol; or

[1R-[1α,2β,3β,4α(1R*,2S*)]]-N-[[2,3-Dihydroxy-4-[7-[N-methyl-(2-phenylcyclopropyl)amino]-5-(propylthio)-3H-[1,2,3]-triazolo[4,5-d]pyrimidin-3-yl] cyclopentyl]methyl]acetamide;

or a pharmaceutically acceptable salt or solvate thereof, or a solvate of such a salt.

10. A pharmaceutical composition comprising a compound according to any one of claims 1 to 9 in combination with a pharmaceutically acceptable diluent, adjuvant or carrier.

11. A method of treatment of a platelet aggregation disorder which comprises administering to a person suffering from such a disorder a therapeutically effective amount of a compound according to any one of claims 1 to 9.

12. A method of treatment of myocardial infarction, thrombotic stroke, transient ischaemic attacks, and/or peripheral vascular disease, which comprises administering to a person suffering from such a condition a therapeutically effective amount of a compound according to any one of claims 1 to 9.

13. A method of treatment of unstable or stable angina which comprises administering to a person suffering from such a condition a therapeutically effective amount of a compound according to any one of claims 1 to 9.

14. A process for the preparation of a compound of formula (I) where $R^1$ is $O(CH_2)_2OH$, which comprises reacting a compound of formula (II):

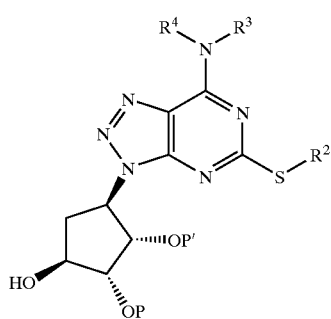

(II)

where $R^2$, $R^3$ and $R^4$ are as defined in claim 1, P and P' are protecting groups, with 2-(2-bromoethoxy)-2H-tetrahydropyran, in the presence of dimethylsulphoxide, a phase transfer catalyst, aqueous sodium hydroxide and a water-immiscible organic solvent, at a temperature of between about 50 and about 120° C., and optionally thereafter removing any protecting groups.

15. A process for the preparation of a compound of formula (I) where $R^1$ is OH, which comprises reacting a compound of formula (XI):

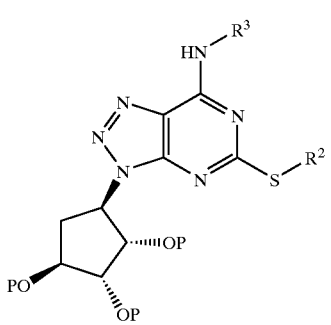

(XI)

where P is a protecting group and $R^2$ and $R^3$ are as defined in claim 1, with a base and an alkylating agent, in an inert dipolar aprotic solvent, at a temperature of between about 20 and about 50° C., and optionally thereafter removing any protecting groups.

16. A process for the preparation of a compound of formula (I) where $R^1$ is $CH_2OH$, which comprises reacting a compound of formula (XVI):

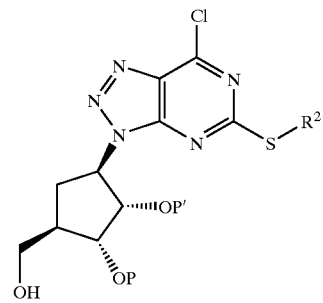

(XVI)

where $R^2$ is as defined in claim 1, P and P' are protecting groups, with $R^3R^4NH$ and a base in a chlorocarbon solvent, at a temperature of between about 20 and about 50° C., and optionally thereafter removing any protecting groups.

17. A process for the preparation of a compound of formula (I) where $R^1$ is $CH_2N_3$, which comprises reacting a compound of formula (XVII):

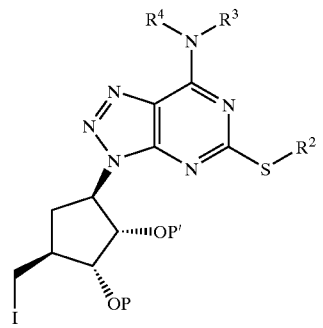

(XVII)

where $R^2$, $R^3$ and $R^4$ are as defined in claim 1 and P and P' are protecting groups, with an alkali metal azide, in an inert chlorocarbon solvent, at a temperature of between about 20 and about 50° C., and optionally thereafter removing any protecting groups.

18. A process for the preparation of a compound of formula (I) where $R^1$ is $CH_2NH_2$, which comprises reducing a compound of formula (I) synthesised as described in claim 17, with hydrogen, in the presence of a transition metal catalyst, in an inert alcoholic solvent, at a temperature of between about 20 and about 50° C., and optionally thereafter removing any protecting groups.

19. A process for the preparation of a compound of formula (I) where $R^1$ is $CH_2NHCOR^9$, which comprises acylating a compound of formula (I) synthesized as described in claim 18, with an acylating agent, in the presence of a base, in an inert chlorocarbon solvent, at a temperature between about 20 and about 50° C., followed by treatment with an alkali metal alkoxide, in an alcoholic solvent, at a temperature between about 20 and about 50° C., and optionally thereafter removing any protecting groups.

20. A compound of formula (II), (XVII), or (XVIII);

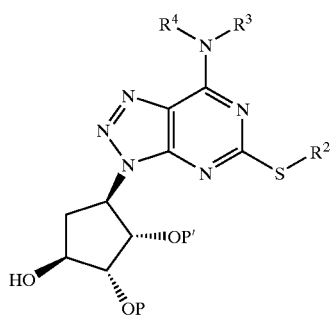

(II)

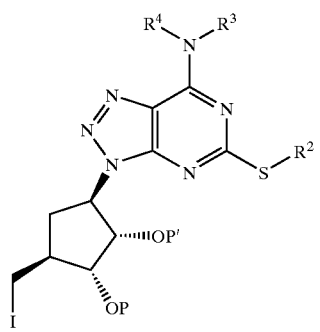

(XVII)

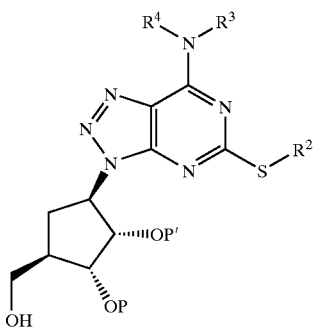

(XVIII)

where $R^2$, $R^3$ and $R^4$ are defined in claim 1, and P and P' are protecting groups.

* * * * *

UNITED STATES PATENT AND TRADEMARK OFFICE
CERTIFICATE OF CORRECTION

PATENT NO. : 6,713,483 B1  Page 1 of 1
DATED : March 30, 2004
INVENTOR(S) : Guile et al.

It is certified that error appears in the above-identified patent and that said Letters Patent is hereby corrected as shown below:

<u>Column 22,</u>
Line 36, "]]3" should read -- ]]-3 --.
Line 51, "[S-[" should read -- [1S-[ --.

Signed and Sealed this

Twenty-fifth Day of May, 2004

JON W. DUDAS
*Acting Director of the United States Patent and Trademark Office*